US009931070B2

(12) United States Patent
Charlez et al.

(10) Patent No.: US 9,931,070 B2
(45) Date of Patent: Apr. 3, 2018

(54) URINE MEASUREMENT DEVICE AND METHOD

(71) Applicant: Observe Medical ApS, Kongens Lyngby (DK)

(72) Inventors: Mikael Charlez, Molndal (SE); Mikael Lofgren, Molndal (SE)

(73) Assignee: Observe Medical ApS, Kongens Lyngby (DK)

( * ) Notice: Subject to any disclaimer, the term of this patent is extended or adjusted under 35 U.S.C. 154(b) by 7 days.

(21) Appl. No.: 14/776,776

(22) PCT Filed: Mar. 14, 2014

(86) PCT No.: PCT/EP2014/055189
§ 371 (c)(1),
(2) Date: Sep. 15, 2015

(87) PCT Pub. No.: WO2014/140328
PCT Pub. Date: Sep. 18, 2014

(65) Prior Publication Data
US 2016/0038070 A1    Feb. 11, 2016

(30) Foreign Application Priority Data
Mar. 15, 2013    (SE) .......................... 1350318

(51) Int. Cl.
*A61B 5/20*    (2006.01)
*G01F 23/26*    (2006.01)

(52) U.S. Cl.
CPC ............ *A61B 5/208* (2013.01); *G01F 23/261* (2013.01); *G01F 23/263* (2013.01);
(Continued)

(58) Field of Classification Search
CPC ..... A61B 5/208; G01F 23/266; G01F 23/263; G01F 23/261; G01F 23/268
See application file for complete search history.

(56) References Cited

U.S. PATENT DOCUMENTS 3,919,455 A      11/1975   Sigdell et al.
5,891,470 A *    4/1999    Rinaldi ................ A61K 9/1635
                                              424/451
(Continued)

FOREIGN PATENT DOCUMENTS

GB       2 417 231 A      2/2006
WO      2010/149708 A1   12/2010

OTHER PUBLICATIONS

International Search Report for corresponding International Application No. PCT/EP2014/055189 dated May 20, 2014.
(Continued)

*Primary Examiner* — Paul West
(74) *Attorney, Agent, or Firm* — RMCK Law Group PLC

(57) ABSTRACT

A urine handling system capsule (105) for releasing an oil mixture in the lumen of a urine handling system, the capsule (105) comprising a capsule wall defining a space filled with an oil mixture, wherein the oil mixture comprises 90-100% of an oil selected from the group consisting of silicone fluids and mineral oils or a mixture thereof, and having a viscosity of at most 600 cSt, and wherein the capsule wall is made of a water-soluble material. A urine measurement system (101) comprising an oil mixture arranged in the luminal space of the measurement system. A method for inhibiting impairment of functionality and measurement accuracy in a urine measurement system comprising applying an oil mixture to the inner surfaces of the urine measurement system. Use of an oil mixture in treatment of luminal surfaces of a urine handling system.

17 Claims, 1 Drawing Sheet

(52) U.S. Cl.
CPC .......... *G01F 23/266* (2013.01); *G01F 23/268* (2013.01); *A61B 2562/18* (2013.01)

(56) References Cited

U.S. PATENT DOCUMENTS

| | | |
|---|---|---|
| 2008/0156092 A1 | 7/2008 | Boiarski |
| 2009/0028811 A1 | 1/2009 | Potter |
| 2011/0146680 A1 | 6/2011 | Conway |
| 2011/0276005 A1 | 11/2011 | Kazutoshi et al. |

OTHER PUBLICATIONS

International Preliminary Report on Patentability for corresponding International Application No. PCT/EP2014/055189 dated Jun. 10, 2015.

\* cited by examiner

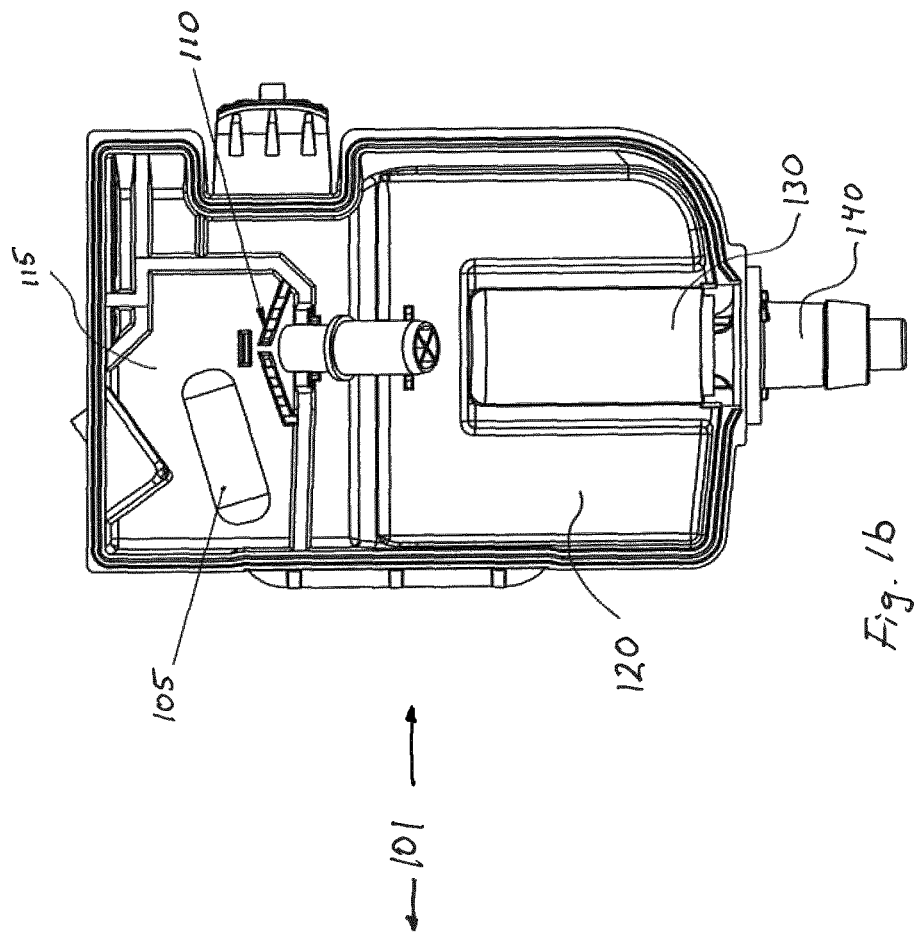
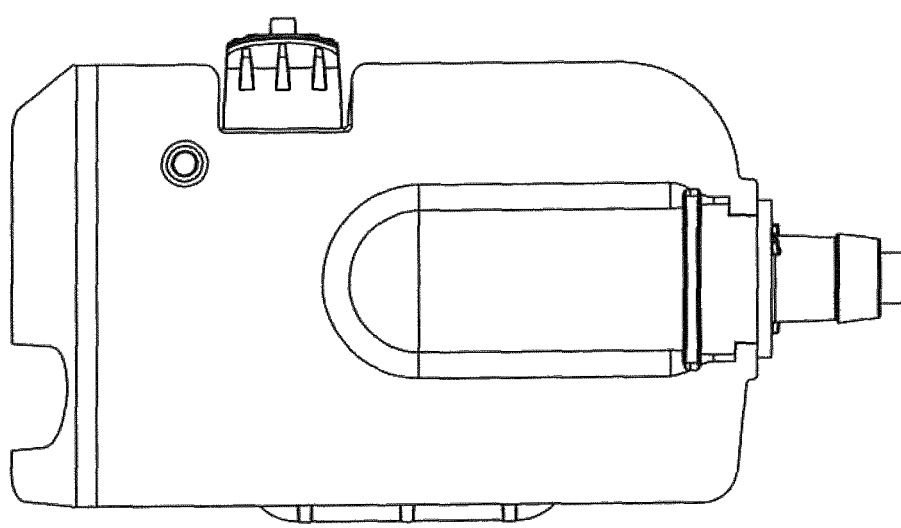

URINE MEASUREMENT DEVICE AND METHOD

This application is a national phase of International Application No. PCT/EP2014/055189 filed Mar. 14, 2014 and published in the English language, which claims priority to Application No. SE 1350318-0 filed Mar. 15, 2013.

TECHNICAL FIELD

The present invention relates to a device and a method for measurement of urine production of a patient wearing a catheter. More specifically it relates to devices and methods for increasing operational time and accuracy of such a device.

BACKGROUND ART

Electronic urine measurement systems are known in the art.

WO 2010/149708 A1 discloses a urine measurement device for measuring urine production of a patient having a urine catheter. The device uses capacitive measurements from electrodes arranged close to a self emptying measurement chamber to calculate the urine level in the measurement chamber.

U.S. Pat. No. 3,919,455 describes a device comprising a siphon chamber for the urine with a self emptying function, and wherein the urine volume is measured with the aid of an optic and/or electric sensor. When the urine level in the siphon chamber increases, the capacitance between two electrodes in the walls of the siphon chamber changes. In this way a signal is created that corresponds to the amount of urine in the siphon chamber. See e.g. FIG. 4 and column 4 lines 34 to 52.

US20110146680A1 discloses a method for manufacturing a silicone catheter wherein the catheter is immersed in oil before it is immersed in a liquid comprising the antimicrobial substance chlorhexidine gluconate in order to make the chlorhexidine gluconate better adhere to the catheter.

SUMMARY OF THE INVENTION

Urine meter systems in general are depending on a connection to a urine catheter in order to get access to the urine-bladder and drain urine from the bladder through a tubing system. The urine is led through a measuring unit and then collected in a collection bag.

Urinary Tract Infection (UTI) is the most common nosocomial infection within the healthcare system today. The UTI extends length of stay, increase costs and contributes to an additional risk to the patients' health status. It's usually related to the installation of said urine catheter. It's revealed through clinical research that the risk of UTI increases by 10% each day the catheter stays in the urinary tract. Bacteria has either their entrance from the outside of the body (64%) or from the very inside (36%).

The inventors have realised, with the aid of literature studies that in in-vitro system bacterial colonisation generates a bio film that becomes mineralised (encrustation). In sterile urine, the development of encrustation has been shown to be dependent on urinary properties such as pH and ionic strength as well as on the biomaterial hydrophobic properties. Urine is generally free from bacteria and thus it is the chemistry of the urine in a measuring and/or collecting environment that dominates the variables. In infected urine, enzyme urease produced by adhered bacteria hydrolyses the urea to produce ammonia. This elevates the urine pH, a condition that favours the precipitation of magnesium and calcium in the form of struvite and hydroxyapatite (HA). These minerals are two major component of encrustation.

Said bio-film and related risk of nosocomial UTIs are not visible to the human naked eye, at least not in the early stages of formation.

Sensor arrangement, signal processing, and signal interpretation methods of signals coming from a capacitive sensor system of a urine measurement system for measuring the urine production of a patient having a urine catheter, may all suffer from harder measuring conditions that are likely to arise over time during prolonged use of such a measuring system.

The inventors have presented the idea that surface degeneration may impair function of a capacitive measuring system and may cause a dysfunction of the siphon portion of the self-emptying chamber. They have conducted experiments around how the presence of a purpose selected oil in the measurement chamber of the siphon system prolongs operational life of the same. They have also suggested that priming of luminal surfaces of the system may be achieved by self-priming with the aid of the urine flowing through the system.

The present invention is providing a device and a method for improving the above mentioned inconveniences by the step(s) of applying a low viscosity oil to the inner surfaces of a urine handling system, with the purpose of arriving at a urine handling system with sustained functional reliability and sustained measurement accuracy, in particular during prolonged use. The effect may be due to the oil influencing factors affecting bacterial growth and bio-film formation. The effect may also come from other mechanisms or from a synergetic effect not yet fully understood.

The present invention discloses a urine handling system of a measurement type having a capacitive sensor system working together with a self emptying measurement chamber and being provided with a capsule of a material that will disintegrate when coming into contact with urine, e.g. a water soluble material. The capsule is initially filled with a purpose selected oil and when the capsule disintegrates the oil is transported with the aid of the urine flow to become applied to those surfaces of the urine handling system that becomes exposed to urine.

The invention is particularly useful in systems that use electronic methods for measuring the amount of urine passing through the system, for example capacitive measurement methods. It will also provide an advantage in systems using self emptying chamber(s) to handle urine measurements. Tests have shown that the self emptying function of such chambers will continue to function reliably for several days, while within a system without the solution of the present invention, functionality may be compromised as soon as after 24 hours.

A urine measurement system according to the present invention thus comprises a well defined measurement chamber for temporarily collecting an amount of urine to measure. The chamber may be of a self emptying siphoning type, that is, the chamber, when it becomes full, empties itself by means of siphoning technique.

Thus, according to a first aspect of the present invention there is provided a urine handling system capsule for releasing an oil mixture in the lumen of a urine handling system, the capsule comprises a capsule wall defining a space filled with an oil mixture, wherein the oil mixture comprises 90-100% of an oil selected from the group consisting of silicone fluids and mineral oils or a mixture thereof, and having a viscosity of at most 600 cSt, and wherein the capsule wall is made of a water-soluble material.

The capsule wherein the water-soluble material is selected from the group consisting of hydroxypropyl methylcellulose and polyvinyl alcohol (PVOH) or a mixture thereof.

The capsule wherein the oil mixture is selected from the group of silicone fluids.

The capsule wherein the oil mixture is selected from the group of linear polydimethylsiloxanes.

The capsule wherein the viscosity of the oil is in the interval of 200 to 600 cSt.

The capsule wherein the viscosity of the oil is in the interval of 300 to 400 cSt.

The capsule wherein the viscosity of the oil is in the interval of 345 to 355 cSt.

The capsule wherein the viscosity of the oil is about 350 cSt.

According to a second aspect of the present invention there is provided a urine measurement system comprising a urine measurement chamber, wherein the urine measurement system comprises an electronic measurement system comprising electrodes arranged outside but close to said measurement chamber to measure changing capacitance values as urine level inside the chamber increases and/or the urine measurement chamber comprises a self-emptying siphoning arrangement arranged to empty itself by means of siphoning technique, wherein an oil mixture is arranged in the luminal space of the urine measurement system, wherein the oil mixture comprises 90-100% of an oil selected from the group consisting of silicone fluids and mineral oils or a mixture thereof, and having a viscosity of at most 600 cSt.

The urine measurement system, wherein the viscosity of the oil is in the interval of 200 to 600 cSt.

The urine measurement system, wherein the viscosity of the oil is in the interval of 300 to 400 cSt.

The urine measurement system, wherein the viscosity of the oil is in the interval of 345 to 355 cSt.

The urine measurement system, wherein the viscosity of the oil is about 350 cSt.

The urine measurement system, wherein the capsule mentioned above is arranged in the luminal space of the measurement system.

The urine measurement system, wherein the capsule is arranged upstream of the measurement chamber or in an upstream portion of the measurement chamber. The urine measurement system, wherein the capsule and possible parts of the capsule wall in early stages of disintegration is prevented from entering a measurement portion of the measurement chamber by a grate.

The urine measurement system wherein the grate is made of a metal or polymer material.

The urine measurement system, wherein the material of the measurement chamber is selected from a group consisting of polymer materials.

The urine measurement system, wherein the material of the measurement chamber is selected from a group consisting of glass materials.

The urine measurement system, wherein the material of the measurement chamber is selected from a group of materials having lipophilic properties.

According to a third aspect of the present invention there is provided a method for inhibiting impairment of functionality and measurement accuracy in a urine measurement system having inner surfaces coming into contact with urine, the method comprising the following steps:

applying an oil mixture to the inner surfaces of the urine measurement system by self-priming with aid of the urine.

The method wherein the method further comprises the step spreading the oil mixture on top of the urine.

The method wherein the urine takes with it the oil mixture when the level of urine in the measurement system increases during filling of the measurement system and thereby the oil mixture is brought in contact with and adheres to the inner surfaces.

The method wherein the oil mixture comprises 90-100% of an oil selected from a group consisting of silicone fluids, and mineral oils, or from a mixture thereof.

The method wherein the oil has a viscosity of at most 600 cSt.

The method wherein the oil has a viscosity in the interval of 200 to 600 cSt.

The method wherein the oil has a viscosity in the interval of 300 to 400 cSt.

The method wherein the oil has a viscosity in the interval of to 355 cSt.

The method wherein the oil has a viscosity of about 350 cSt.

The method wherein the oil mixture is applied by connecting a patient's urinary catheter with the urine measurement system mentioned above provided with the capsule mentioned above.

According to a fourth aspect of the present invention there is provided a use of an oil mixture in treatment of luminal surfaces of a urine handling system, wherein the oil mixture comprises 90-100% of an oil selected from the group consisting of silicone fluids and mineral oils or a mixture thereof, and having a viscosity of at most 600 cSt.

The above use, wherein the viscosity is in the interval of 200 to 600 cSt.

The above use, wherein the viscosity is in the interval of 300 to 400 cSt.

The above use, wherein the viscosity is in the interval of 345 to 355 cSt.

The above use, wherein the viscosity is in the interval of 345 to 355 cSt.

The above use, wherein the viscosity is about 350 cSt.

The above use, wherein the oil mixture is an oil mixture void of antimicrobial agent.

BRIEF DESCRIPTION OF THE DRAWINGS

The invention will now be further explained with the aid of one or more embodiments of the invention in conjunction with the accompanying drawings of which:

FIG. 1a is a front view of a measurement chamber of a urine handling system.

FIG. 1b is view of the measurement chamber of FIG. 1a wherein a front wall is removed exposing the inner structure including capsule/oil pill arrangement and grate arrangement.

DETAILED DESCRIPTION

Definitions

In the context of the present invention the following terms and phrases will be used having the following meanings:

A "urine handling system" denotes a system for handling of urine emanating from a human patient involved in a care situation, including but not limited to, a nursing situation and a treatment situation.

A "urine measurement system" denotes a system designed to measure the amount of urine emanating from a human patient involved in a care situation, including but not limited to, a nursing situation and a treatment situation.

The term "silicone fluid" is intended to include silicone oils such as silicone esters or other liquid silicone compounds with the general formula:

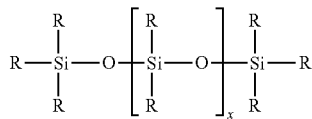

where each R can be an aliphatic group such as an alkyl group, for example a methyl, ethyl or propyl radical or alkoxy group or a phenyl group, or combinations thereof; and
where x has a value of from about 0 to about 10,000, preferably from about 1 to about 200, and most preferably from about 10 to about 125.

The Problem

Urine is a body liquid that may be very aggressive on manmade surfaces, in particular on surfaces inside a urine measurement system. The urine measurement system according to the invention may be a closed system that comprises a tubing system connected to a patient's catheter, a measurement chamber and a collection bag. The urine measurement system is located outside the body of a patient. The tubing system leads the urine from the urine bladder to the measurement chamber where a capacitive, contact-less sensor system senses the signals through the wall of the measurement chamber, and thereof calculates the volume. The chamber wall is preferably of a rigid polymeric material, easily obtained in medical equipment grades. The urine is preferably collected in a collection bag after it has been measured. Such a collection bag is preferably made of a flexible polymeric material, and has a volume considerably larger than the volume of the measurement chamber.

The measurement chamber is preferably devised to self-empty at a certain volume around 15-20 ml. The challenge in said self-emptying measurement chamber is to handle the effects of degenerative process compromising the electric and physical properties of the delicate surfaces of the measurement chamber caused by the urine over time.

Thus, and as also mentioned above, the inventor has realised, and also experience, that within an unforeseeable amount of time there is a decrease of signal through the measurement chamber wall that seems to be caused by a bio film formation on the surface(s) corresponding to where the sensors are arranged. There seems to be a considerable risk of a degeneration of the delicate surfaces within the region of the self-emptying system which may lead to a dysfunction of the self-emptying mechanism.

One solution to the problem would be to replace the chamber when signs of dysfunction are noticeable. However, it would be an advantage if this could be avoided, since it requires more resources.

The Solution

Now turning to FIGS. 1a and 1b, the present invention teaches to apply a substance to the surfaces of the urine measurement system to improve sustained measurement functionality and accuracy.

If a urine measurement system provided with a measurement chamber 101 comprising a siphoning self-emptying arrangement begins to execute premature emptying sequences, it is likely that surface(s) of the measurement chamber 101 critical to initiation of the self-emptying sequence, has become compromised. The solution involves arranging an oil releasing device 105 early in the flow path of the urine measurement system, and to let said oil releasing device 105 release oil into the system for adhering to the luminal surfaces of the system. Subsequent to release the urine, as being a watery, oil repellant fluid, aids in dispersing the oil, which oil gets on top of the urine, and during a filling phase of the measurement chamber, takes with it the oil, which oil adheres to the luminal surfaces in need thereof.

It is realised by the skilled reader that this measure of providing an oil releasing device would improve not only a urine measurement system, but any urine handling system liable or susceptible to degradation over time.

The present invention relates to a method for improving sustained functionality and measurement accuracy in a urine measurement system having inner surfaces coming into contact with urine, the method comprising the following step(s):
  applying an oil mixture to the inner surfaces of the urine measurement system.

By improving sustained functionality and measurement accuracy, impairment of functionality and measurement accuracy is inhibited.

Thus, the present invention relates to a method for inhibiting impairment of functionality and measurement accuracy in a urine measurement system having inner surfaces coming into contact with urine, the method comprising the following step(s):
  applying an oil mixture to the inner surfaces of the urine measurement system.

The oil mixture is preferably applied to inner surfaces of the urine measurement system by self-priming with aid of the urine. The oil mixture may be applied to inner surfaces of the urine measurement system by self-priming with aid of the urine flowing through the system.

The method may comprise the step spreading the oil mixture on top of the urine. This step may be performed before the step applying an oil mixture to the inner surfaces of the urine measurement system.

In one embodiment, the oil mixture is applied to the inner surfaces of the urine measurement system when the level of urine in the urine measurement system increases. This may be combined with the step spreading the oil mixture on top of the urine. This is a way to achieve self-priming of the inner surfaces with the oil mixture aided by the urine.

In one embodiment, the urine takes with it the oil mixture when the level of urine in the measurement system increases during filling of the measurement system and thereby the oil mixture is brought in contact with and adheres to the inner surfaces.

The urine may take with it the oil mixture when the level of urine in a measurement chamber of the measurement system increases during filling of the measurement chamber and thereby the oil mixture is brought in contact with and adheres to the inner surfaces.

The method may comprise the step adhering the oil mixture to the inner surfaces. This step may be performed in combination with and after the step spreading the oil mixture on top of the urine. This is a way to achieve self-priming of the inner surfaces with the oil mixture aided by the urine.

The oil mixture may be spread on top of the urine, brought into contact with the inner surfaces by the urine and adhere to the inner surfaces. Thereby, the oil mixture is applied to the inner surfaces of the urine measurement system by self-priming. The urine may take with it the oil mixture when the level of urine in the measurement system increases during filling of the measurement system and thereby the oil mixture is brought in contact with and adheres to the inner surfaces.

The oil mixture may be applied to the inner surfaces of the urine measurement system by providing a water-soluble capsule in the urine handling system. The water-soluble capsule may be provided in the urine handling system upstream of a measurement portion and a siphoning portion of a urine measurement chamber of the system.

When the oil mixture has been released the oil mixture is spread on top of the urine, since urine is a watery and oil repellent fluid. The oil mixture forms a layer on top of the urine. When the amount of urine in the urine measurement system and thus the level of urine in the urine measurement system increases the oil mixture that is floating on top of the urine is brought in contact with the inner surfaces of the urine measurement system. The oil mixture adheres to the inner surfaces and is applied to the inner surfaces. Thereby, the oil mixture is applied to the inner surfaces before the urine reaches higher levels of the inner surfaces. Thus, the oil mixture prevents or at least makes it more difficult for the urine to come into direct contact with the inner surfaces of the urine measurement system. The oil mixture is moved by the urine when the level of urine increases and thereby the oil mixture is applied to the inner surfaces of the urine measurement system just before the urine reaches a higher level in the urine measurement system. Thus, the inner surfaces are freshly coated with the oil mixture when the urine reaches the inner surfaces. After emptying of the urine measurement system, the oil mixture is applied again on the inner surfaces before the urine reaches the inner surfaces. Thus, the inner surfaces are always freshly coated with the oil mixture when urine reaches the inner surfaces. Thereby, an improved resistance against degeneration of the inner surfaces of the urine measurement system. Consequently, the functionality of the urine measurement system, such as the functionality of the siphoning self-emptying arrangement, is improved. For example is the degradation of the surfaces of the siphoning self-emptying arrangement inhibited and thus the siphoning effect is maintained. The functionality over time is improved and impairment of the functionality is inhibited. Also the measurement accuracy of the urine measurement system, such as the measurement accuracy of the capacitive measurement system, is improved. For example is the degradation of the surfaces of the wall of the measurement chamber through which the capacitive measurement system senses signals inhibited and thus the sensing ability is maintained. The measurement accuracy over time is improved and impairment of the measurement accuracy is inhibited.

The urine measurement system may comprise a urine measurement chamber. The urine measurement system may comprise electrodes arranged outside but close to the measurement chamber. The electrodes may be arranged to measure changing capacitance values as urine level inside the chamber increases. The electrodes may be arranged on the outside of the measurement chamber. The electrodes may be arranged on the outer surface of the measurement chamber. The electrodes may be integrated in the measurement chamber. The electrodes may be integrated in the measurement chamber on the outside of the measurement chamber.

In one embodiment, the present invention relates to a urine measurement system comprising a urine measurement chamber, wherein the urine measurement system comprises an electronic measurement system comprising electrodes arranged outside but close to said measurement chamber to measure changing capacitance values as urine level inside the chamber increases, wherein an oil mixture is arranged in the luminal space of the urine measurement system, wherein the oil mixture comprises 90-100% of an oil selected from the group consisting of silicone fluids and mineral oils or a mixture thereof, and having a viscosity of at most 600 cSt.

In one embodiment, the present invention relates to a urine measurement system comprising a urine measurement chamber, wherein the urine measurement chamber comprises a self-emptying siphoning arrangement arranged to empty itself by means of siphoning technique, wherein an oil mixture is arranged in the luminal space of the urine measurement system, wherein the oil mixture comprises 90-100% of an oil selected from the group consisting of silicone fluids and mineral oils or a mixture thereof, and having a viscosity of at most 600 cSt. The self-emptying siphoning arrangement may be arranged to empty itself by means of siphoning technique when a certain volume of urine is present in the urine measurement chamber.

In one embodiment, the present invention relates to a urine measurement system comprising a urine measurement chamber and an electronic measurement system comprising electrodes arranged outside but close to said measurement chamber to measure changing capacitance values as urine level inside the chamber increases, wherein the capsule of the present invention is arranged in the luminal space of the measurement system.

In one embodiment, the present invention relates to a urine measurement system comprising a urine measurement chamber, wherein the urine measurement chamber comprises a self-emptying siphoning arrangement arranged to empty itself by means of siphoning technique, wherein the capsule of the present invention is arranged in the luminal space of the measurement system. The self-emptying siphoning arrangement may be arranged to empty itself by means of siphoning technique when a certain volume of urine is present in the urine measurement chamber.

In one embodiment the present invention relates to a urine measurement system comprising a urine measurement chamber, wherein the urine measurement system comprises an electronic measurement system comprising electrodes arranged outside but close to said measurement chamber to measure changing capacitance values as urine level inside the chamber increases and the urine measurement chamber comprises a self-emptying siphoning arrangement arranged to empty itself by means of siphoning technique, wherein the capsule of the present invention is arranged in the luminal space of the measurement system.

Capsule

The oil releasing device is preferably implemented as a capsule 105 comprising a capsule wall made of a water-soluble material. The capsule encapsulates an amount of oil. The capsule is preferably of a shape selected from the group of cylindrical, cylindrical with hemispherical ends, spherical, oval, elliptical or of a shape rounded cubic or tablet, or of any shape suitable to the purpose.

The material of the capsule wall is a water-soluble material, preferably one that disintegrates in a few minutes when exposed to urine flow. One preferred material of the capsule wall is polyvinyl alcohol (PVOH). Most preferred, however, the material of the capsule wall is hydroxypropyl methylcellulose, such as for example the material of LICAPS capsules from CAPSUGEL—www.capsuqel.com. One particular advantage of PVOH is a very quick release of the oil because of fast disintegration. One advantage of hydroxypropyl methylcellulose is its stability which facilitates handling, storage and transportation.

In one embodiment, the material of the capsule wall disintegrates within one hour. Thereby, the material of the capsule wall is disintegrated within one hour after is has been exposed to urine. This has the advantage that the oil mixture in the capsule is rapidly released and the thus the protection of the inner surfaces of the urine handling system is rapidly established. The material of the capsule wall may disintegrate within 30 minutes after exposure to urine, such as within 15 minutes, such as within 10 minutes, such as within about 5 minutes. The material of the capsule wall may disintegrate within a few minutes. The material of the capsule wall may disintegrate within a few minutes after exposure to urine. The material of the capsule wall is preferably totally disintegrated within the above specified time intervals.

In addition to improved measurement accuracy and operational life of the measurement chamber, the capsule allows that the oil, as an active ingredient, is inactive during shelf life and activated first in the clinical setting.

The capsule provides a convenient way of storing and handling the oil mixture during transport and storage of a urine measurement system. The capsule also provides a convenient way of activating the protection of the inner surfaces of the urine measurement system in the clinical situation, i.e. when the urine measurement system is to be put in operation. The capsule can be stored in the urine measurement system or separately up until use of the urine measurement system. Since the oil mixture not is applied to the inner surfaces of the urine measurement before use of the urine measurement system, the protection of the oil mixture provided to the inner surfaces is not damaged or deteriorated before use of the urine measurement system. If not stored in the urine measurement system, the capsule is inserted in the urine measurement system before use. When the urine measurement is to put into use, the urine that is entering the urine measurement system dissolves the water-soluble material of the capsule wall releasing the oil mixture. The oil mixture is transported with the urine into the measurement chamber and the oil mixture is thereby distributed into the measurement chamber. The water-soluble material is preferably disintegrated in a few minutes when exposed to urine in order to release the oil mixture rapidly and to rapidly establish the application of the oil mixture on the inner surfaces of the urine measurement surface aided by the urine as described above. Thereby, the protection of the inner surfaces of the urine measurement system is rapidly established.

To prevent the capsule from interfering with urine flow in the measurement chamber it is advantageous to provide a grate 110 or similar arrangement to prevent early, non dissolved fragments of the capsule to clog the flow of urine. It is also advantages to provide such a grate to confine the capsule during transport and pre-use to an upper portion of the measurement chamber.

Thus, the grate 110 is arranged to prevent pieces of non-dissolved capsule from travelling with the urine flow and temporarily blocking possible valves or siphoning system. The term "measurement chamber" may be used as a general term denoting the whole chamber comprising a first portion 115, i.e., an inlet upstream portion or "atrium", a second portion 120 midstream which is the actual measurement portion of the measurement chamber presenting important surfaces for the sensors. Further downstream is provided a third portion 130, 140 providing the self-emptying siphoning arrangement 130 and outlet piping 140. To be able to treat the surfaces of the second portion 120 and the third portion 130 with oil from the capsule, the capsule is provided in the first portion 115, the atrium. The grate 110 is arranged between the atrium 115 and the second portion 120 of the measurement chamber 101.

Oil

The oil is a purpose selected oil. Viscosity may be at most 600 centiStoke (cSt, $mm^2/s$). Viscosity is preferably in the interval of 200 to 600 centiStoke (cSt, $mm^2/s$). Viscosity is more preferred in the interval of 300 to 400 centiStoke (cSt, $mm^2/s$). Viscosity is even more preferred in the interval of 345 to 355 centiStoke (cSt, $mm^2/s$). An oil having a viscosity of at most 600 cSt or within these intervals is spread on top of urine and forms a layer of the oil on top of the urine. The oil is spread over the surface of the urine. An oil having such viscosities is spread on top of the urine, is brought in contact with the inner surfaces of the urine measurement system and is applied to the inner surfaces of the urine measurement system in the way described above. A too high viscosity will result in that oil not is spread over the surface of urine and thereby not is brought in contact with inner surfaces of a urine measurement system and nor is applied to inner surfaces of a urine measurement system. Instead an oil having a too high viscosity will accumulate and form a clump.

The oil is preferably of a grade approved for medical use. It is preferably an oil comprising as a major constituent an oil preferably selected from the group of silicone fluids or mineral oils or from a combination thereof.

The silicon oil is preferably selected from polydimethylsiloxanes, polymethylphenylsiloxanes, polydipropylsiloxanes, and polyphenylsiloxanes. More preferably the silicon oil is selected from polydimethylsiloxanes. More preferred is an oil composition selected from the group of linear polydimethylsiloxanes, such as for example SILBIONE oil 70047 V 350 from Bluestar Silicones—www.blustarsilicones.com. Most preferred is an oil comprising 90-100% silicone oil of viscosity about 350 cSt. The oil may be free of additive, or may comprise one or more additives.

The volume of oil provided in the capsule to achieve the described has been tested and effect is achieved with a volume of 0.5 ml of oil.

The capacitive sensors are not influenced, or being influenced only negligible by the oil mixture.

Oil Treatment

The inventors have also generalised that the purpose selected oil disclosed above may be applied to urine handling system surfaces using other methods than by capsule. Thus a specific use of the oil is made an object of the present invention;

It is disclosed the use of a compound X in the application Y, wherein the compound X is an oil mixture comprising 90-100% of an oil selected from the group consisting of silicone fluids and mineral oils or a mixture thereof, and having a viscosity of at most 600 cSt, preferably within the interval of 300 to 400 cSt, more preferred within the interval of 300 to 400 cSt, even more preferred 345 to 355 cSt, and most preferred about 350 cSt, and wherein the application Y is the treatment of luminal surfaces of a urine handling system or a urine measurement system. With the term "treatment" is here meant an activity wherein the oil is applied to the surface in question regardless of the method of distribution of the oil into the luminal space of the urine handling system. Preferred methods include pouring oil into the luminal space, spraying, painting, immersion, soaking, releasing, and distribution with the aid of a watery fluid. The watery fluid may be urine. In particular is distribution involving release of the oil mixture from a capsule as described above preferred and more preferred is distribution from such a capsule where the released oil mixture is transported into the luminal space with the urine. Regardless of the method of distribution of the oil mixture into the luminal space, the oil mixture may be applied to the luminal surfaces of the urine handling system by self-priming as described above.

In the present invention the oil treatment as described is taught as single step of treatment of the surfaces for increased operational time. The oil is a non-complex compound involving no other substance, like an antimicrobial agent, such as for example chlorhexidine. It is an advantage that no other substance, like an antimicrobial agent, such as for example chlorhexidine, is needed. The oil mixture may advantageously be void of such antimicrobial substance. This is also true regarding the oil mixture when released by capsule.

Material of Measurement Chamber

The material of the measurement chamber is preferably a polymer of medical equipment grade. More preferred the material of the measurement chamber is a polymer of medical equipment grade, wherein the polymer exhibits a lipophilic surface. Most preferred the material of the measurement chamber is polypropylene. Tests have shown that lipophilic material keep the oil at the chamber surface, in contrast to a lipophobic material which will repel the oil. Thus, with a lipophobic material the oil would be washed away by the urine rather quickly by time.

Examples/Tests

The following table illustrates a combination of capsule material, oil, and measurement chamber material.

| EXAMPLE | Capsule material | Oil/viscosity | Chamber material | Prolonged operational time (%) |
| --- | --- | --- | --- | --- |
| EX A | hydroxypropyl methylcellulose | Silicone/ 350 cSt | polypropylene | 480 to 840 |

A series of tests with a urine measurement system having an electronic measurement system and a self-emptying siphoning arrangement have been performed. The time until surface degradation in the form of biofilm formation were determined by measuring the time until either the electronic measurement signal is unsatisfactory or disappears or until the function of the self-emptying siphoning arrangement is unsatisfactory or ceases. The material of the measurement chamber of the measurement system is polypropylene. Tests were performed with and without oil. In tests involving an oil, the oil was supplied by means of a capsule. The oil as well as the material of the capsule wall is specified in the table above. Two different samples of urine were tested and the results are presented below.

| | | Time until surface degradation in hours | |
| --- | --- | --- | --- |
| Test number | Urine sample | With oil | Without oil |
| 1 | 1 | 479 | |
| 2 | 1 | | 68 |
| 3 | 1 | | 68 |
| 4 | 1 | | 57 |
| 5 | 1 | | 74 |
| 6 | 2 | 336 | |
| 7 | 2 | | 70 |
| 8 | 2 | | 58 |

For urine sample 1 the operational time until surface degradation increased from 57-74 hours without oil to 479 hours when having an oil present, which corresponds to an prolonged operational time of 650-840%. For urine sample 2 the operational time until surface degradation increased from 58-70 hours without oil to 336 hours when having an oil present, which corresponds to an prolonged operational time of 480-580%.

The invention claimed is:

1. A urine measurement system comprising a urine measurement chamber,
    wherein the urine measurement system comprises:
        an electronic measurement system comprising:
        i. electrodes arranged outside said measurement chamber to measure changing capacitance values as urine level inside the chamber increases;
        wherein the urine measurement chamber comprises:
        ii. a self-emptying siphoning arrangement arranged to empty itself by means of siphoning technique,
    a capsule for releasing an oil mixture, wherein the capsule is arranged in the luminal space of the urine measurement system, wherein the capsule comprises a capsule wall defining a space filled with the oil mixture, wherein the oil mixture comprises 90-100% of an oil selected from the group consisting of silicone fluids and mineral oils or a mixture thereof, and having a viscosity of at most 600 cSt, and wherein the capsule wall is made of a water-soluble material.

2. The urine measurement system according to claim 1, wherein the water-soluble material is selected from the group consisting of hydroxypropyl methylcellulose and polyvinyl alcohol (PVOH) or a mixture thereof.

3. The urine measurement system according to claim 1, wherein the oil mixture is selected from the group of silicone fluids.

4. The urine measurement system according to claim 3, wherein the oil mixture is selected from the group of linear polydimethylsiloxanes.

5. A urine measurement system according to claim 1, wherein the viscosity of the oil is in the interval of 200 to 600 cSt.

6. The urine measurement system according to claim 1, wherein the capsule is arranged upstream of the measurement chamber or in an upstream portion of the measurement chamber and is prevented from entering the measurement chamber by a grate.

7. The urine measurement system according to claim 6, wherein the grate is made of a metal or polymer material.

8. The urine measurement system according to claim 1, wherein the material of the measurement chamber is selected from a group consisting of polymer materials.

9. The urine measurement system according to claim 1, wherein the material of the measurement chamber is selected from a group consisting of glass materials.

10. The urine measurement system according to claim 1, wherein the material of the measurement chamber is selected from a group of materials having lipophilic properties.

11. A method for inhibiting impairment of functionality and measurement accuracy in a urine measurement system comprising a urine measurement chamber having inner surfaces coming into contact with urine, the method comprising the following step(s):
applying an oil mixture to the inner surfaces of the urine measurement chamber by providing a water-soluble capsule, which disintegrates when exposed to a urine flow, in the urine measurement system, wherein the capsule comprises a capsule wall defining a space filled with the oil mixture, and wherein the capsule wall is made of a water-soluble material.

12. The method according to claim 11, wherein the method comprises the step spreading the oil mixture on top of the urine.

13. The method according to claim 11, wherein, the oil mixture is applied to the inner surfaces of the urine measurement system when the level of urine in the urine measurement system increases.

14. The method according to claim 11, wherein the urine takes with it the oil mixture when the level of urine in the urine measurement system increases during filling of the measurement system and thereby the oil mixture is brought in contact with and adheres to the inner surfaces.

15. The method according to claim 11, wherein the oil mixture comprises 90-100% of an oil selected from a group consisting of silicone fluids, and mineral oils, or from a mixture thereof.

16. The method according to claim 11, wherein the oil has a viscosity of at most 600 cSt.

17. The method according to claim 11, wherein the oil mixture is applied by connecting a patient's urinary catheter with the urine measurement system comprising the urine measurement chamber, wherein the urine measurement system comprises:
an electronic measurement system comprising:
i. electrodes arranged outside said urine measurement chamber to measure changing capacitance values as urine level inside the chamber increases;
wherein the urine measurement chamber comprises:
ii. a self-emptying siphoning arrangement arranged to empty itself by means of siphoning technique,
wherein the capsule for releasing an oil mixture is arranged in the luminal space of the urine measurement system, wherein the oil mixture comprises 90-100% of an oil selected from the group consisting of silicone fluids and mineral oils or a mixture thereof, and having a viscosity of at most 600 cSt.

* * * * *